(12) United States Patent
Lenaerts et al.

(10) Patent No.: US 10,709,066 B2
(45) Date of Patent: Jul. 14, 2020

(54) DEVICE FOR ANALYZING THE COMPOSITION OF A GRAIN-MOG MIXTURE

(71) Applicant: CNH Industrial America LLC, New Holland, PA (US)

(72) Inventors: Bart Lenaerts, Zutendaal (BE); Bart M. A. Missotten, Herent (BE); Karlien D'huys, Alken (BE)

(73) Assignee: CNH Industrial America LLC, New Holland, PA (US)

( * ) Notice: Subject to any disclaimer, the term of this patent is extended or adjusted under 35 U.S.C. 154(b) by 154 days.

(21) Appl. No.: 15/238,757

(22) Filed: Aug. 17, 2016

(65) Prior Publication Data
US 2017/0049050 A1 Feb. 23, 2017

(30) Foreign Application Priority Data
Aug. 19, 2015 (BE) .................................. 2015/5517

(51) Int. Cl.
*A01D 41/127* (2006.01)
*G01N 25/00* (2006.01)
(Continued)

(52) U.S. Cl.
CPC ........... *A01D 41/127* (2013.01); *A01D 41/12* (2013.01); *A01F 12/46* (2013.01); *A01F 12/60* (2013.01); *G01J 5/10* (2013.01); *G01N 25/00* (2013.01); *G01N 33/10* (2013.01); *H04N 5/33* (2013.01); *G01J 2005/0077* (2013.01)

(58) Field of Classification Search
None
See application file for complete search history.

(56) References Cited

U.S. PATENT DOCUMENTS 5,480,354 A * 1/1996 Sadjadi ............. A01D 41/1271
460/149
8,045,168 B2 * 10/2011 Missotten ............. G01N 21/85
356/445
(Continued)

FOREIGN PATENT DOCUMENTS

CN 103592316 A 2/2014
DE 4317513 A1 12/1994
(Continued)

*Primary Examiner* — Christopher G Findley
(74) *Attorney, Agent, or Firm* — Peter Zacharias; Patrick Sheldrake

(57) ABSTRACT

A method for analyzing the composition of a grain-MOG mixture comprising a kernel fraction and an MOG-fraction. The method includes steps of receiving a grain-MOG mixture, at a thermal excitation location, subjecting a sample volume of the grain-MOG mixture to a thermal excitation using a thermal excitator, generating a thermal image at an imaging location of at least a surface of the sample volume of the grain-MOG mixture that has been subjected to the thermal excitation, processing the thermal image and therewith obtaining data representing the temperature distribution over the thermal image, and relating the temperature distribution to the share of the kernel fraction in the grain-MOG mixture. A device for analyzing the composition of a grain-MOG mixture comprising a kernel fraction and an MOG-fraction is also provided.

20 Claims, 5 Drawing Sheets

(51) Int. Cl.
*A01D 41/12* (2006.01)
*G01N 33/10* (2006.01)
*A01F 12/46* (2006.01)
*A01F 12/60* (2006.01)
*G01J 5/10* (2006.01)
*H04N 5/33* (2006.01)
*G01J 5/00* (2006.01)

(56) References Cited

U.S. PATENT DOCUMENTS

| | | |
|---|---|---|
| 8,139,824 B2 | 3/2012 | Missotten et al. |
| 8,831,292 B2 | 9/2014 | Brueckner et al. |
| 9,779,330 B2 * | 10/2017 | Wellington .......... G06K 9/6267 |
| 2004/0020831 A1 | 2/2004 | Meinlschmidt et al. |
| 2008/0144049 A1 | 6/2008 | Ringermacher et al. |

FOREIGN PATENT DOCUMENTS

| | | | |
|---|---|---|---|
| WO | 03058215 A1 | 7/2003 | |
| WO | WO 2007007165 A2 * | 1/2007 | .......... B07C 5/3425 |
| WO | 2010063866 A1 | 6/2010 | |

* cited by examiner

DEVICE FOR ANALYZING THE COMPOSITION OF A GRAIN-MOG MIXTURE

CROSS REFERENCE TO RELATED APPLICATION

This application claims priority to Belgium Application No. 2015/5517, filed Aug. 19, 2015, the contents of which are incorporated herein by reference.

FIELD OF THE INVENTION

The invention pertains to a method for determining the composition of a grain-MOG mixture. The invention also pertains to a device for analyzing the composition of a grain-MOG mixture comprising a kernel fraction and an MOG-fraction.

BACKGROUND OF THE INVENTION

"MOG" is widely used in the art to refer to "material other than grain".

Agricultural harvesters comprise a processing device that comprises a thresher. Harvested crop is introduced into the processing device in a raw form, in which stalks may still be present and the grain is still in the ears. The thresher separates grain kernels from other plant parts, such as stalks, ears, husks and the like. The threshed grain leaves the processing device to be transported to a storage facility, such as a grain tank. The separated MOG is discharged from the agricultural harvester. Often, the processing device additionally comprises one or more sieves, to improve the separation between grain kernels and MOG, with the objective to transport a little chaff and other undesired material to the grain tank along with the threshed grain.

The effectiveness and efficiency of threshing is not easy to control as it depends on many variables and because it is hard to measure.

US2009/0297040 discloses a method and device for crop particle discrimination. This device and method can be used to determine how much chaff is present in the grain-MOG mixture that travels from the processing device to the grain tank. If too much chaff is present, the processing device is likely in need of re-adjustment of some of the processing parameters.

In US2009/0297040, an optical method is proposed to discriminate between grain kernels and chaff. It relies on the difference in reflectivity of the grain kernel and the chaff

SUMMARY OF THE INVENTION

It is advantageous to provide a method for analyzing the composition of a grain-MOG mixture, in particular for determining the share of the kernel fraction of a grain-MOG mixture. In accordance with an aspect of the present invention, there is provided a method for analyzing the composition of a grain-MOG mixture comprising a kernel fraction and an MOG-fraction. The method includes steps of receiving a grain-MOG mixture, at a thermal excitation location, subjecting a sample volume of the grain-MOG mixture to a thermal excitation using a thermal excitator, generating a thermal image at an imaging location of at least a surface of the sample volume of the grain-MOG mixture that has been subjected to the thermal excitation, processing the thermal image and therewith obtaining data representing the temperature distribution over the thermal image, and relating the temperature distribution to the share of the kernel fraction and/or the MOG-fraction in the grain-MOG mixture.

The grain-MOG mixture to be examined comprises kernels and other material. Other material in the grain-MOG mixture is for example chaff. Other plant materials such as parts of the ears and fragments of stalks or leaves may be present as well but in general the grain-MOG mixture will mainly be made up out of grain kernels and chaff.

A special component that can be present in the grain-MOG mixture are "whitecaps". A "whitecap" is a piece of chaff in which a grain kernel is still present. So, in the threshing process the grain kernel is separated from the ear, but the separation between kernel and chaff did not take place.

With many known techniques for discriminating between grain kernels and MOG such as chaff, whitecaps cannot properly be detected. For example, with the method that is disclosed in US2009/0297040, whitecaps will be seen as chaff, because of the reflectivity of the chaff piece that still surrounds the kernel of the whitecap.

In accordance with another aspect of the present invention, a sample volume of the grain-MOG mixture is analyzed in order to determine the share of kernels in the mixture.

Kernels and materials other than grain, e.g. chaff, have a different heat capacity. At a given supply of thermal energy, the temperature change of a kernel is different from the temperature change of e.g. a piece of chaff. In general, a piece of chaff will heat up faster than a kernel.

This principle is used to distinguish between kernels and material other than grain in the grain-MOG mixture.

In accordance with still another aspect of the present invention, after receiving a grain-MOG mixture, a sample volume of the grain-MOG mixture is subjected to a thermal excitation, e.g. the sample volume is heated or cooled. As e.g. heat will always penetrate into the grain-MOG mixture to some extent, it will be a volume of the grain-MOG mixture that is subjected to thermal excitation. The sample volume can be a part of the grain-MOG mixture or all of the grain-MOG mixture.

The thermal excitation takes place at a thermal excitation location.

The thermal excitation is carried out using a thermal excitator, which can be e.g. a heater, a cooler or a combined heater/cooler. Alternatively, other types of thermal excitation are used, e.g. induction or microwaves. The thermal excitator optionally comprises a thermal energy source, which is for example point-shaped, line-shaped or area-shaped.

By thermal excitation of the grain-MOG mixture, temperature differences between kernels and material other than grain are created.

At a subsequent step in the method, a thermal image is generated of at least a surface of the sample volume of the grain-MOG mixture that has been subjected to the thermal excitation. This thermal image is generated at an imaging location. The imaging location may be different from the thermal excitation location or the imaging location may be the same as the thermal excitation location. The temperature difference between the kernels and the material other than grain that result from the thermal excitation will be captured on the thermal image that is generated.

A subsequent step in the method is processing the thermal image and therewith obtaining data representing the temperature distribution over the thermal image. In this step, data relating to local temperature differences in the sample volume that is imaged becomes available.

Then, the temperature distribution in the sample volume of the grain-MOG mixture is related to the share of the kernel fraction in the grain-MOG mixture. This is for example done by obtaining the percentage of the total area of the thermal image that has a temperature that generally corresponds to the temperature that—given the amount of transferred thermal energy in the thermal excitation—can be expected for the kernels.

Optionally, in addition or alternatively, the temperature distribution in the sample volume of the grain-MOG mixture is related to the share of the MOG-fraction in the grain-MOG mixture. This is for example done by obtaining the percentage of the total area of the thermal image that has a temperature that generally corresponds to the temperature that—given the amount of transferred thermal energy in the thermal excitation—can be expected for the kernels.

The method provides an elegant and efficient way of determining the share of kernels and/or MOG in a grain-MOG mixture.

In a possible embodiment, multiple subsequent thermal images are generated of at least a surface of the sample volume of the grain-MOG mixture that has been subjected to the thermal excitation. This allows taking the temperature profile of the kernel fraction and/or of the MOG-fraction in response to the thermal excitation into account when making the distinction between the kernels and the MOG. This increases the accuracy and the reliability of the analysis, as kernels and MOG show a different temperature profile in response to thermal excitation.

As already mentioned, in a possible embodiment, the imaging location and the thermal excitation location coincide with each other. i.e. the imaging location is the same as the thermal excitation location. Optionally, in such an embodiment, thermal excitation and thermal imaging take place simultaneously.

In a possible embodiment, the grain-MOG mixture is moved along a grain-MOG mixture path. In this embodiment, the thermal excitation location and the imaging location are located along the grain-MOG mixture path. They can be at the same location or at different locations. When the thermal excitation location and the imaging location are at different location, then the imaging location can be directly downstream of the thermal excitation location (seen in the direction of transport of the grain-MOG mixture along the grain-MOG mixture path) or the thermal excitation location and the imaging location can be spaced apart from each other.

In a possible embodiment, the thermal excitation is carried out in a modulated way, in the form of a pulse, in the form of a square pulse, in the form of a sinusoidal wave, or in the form of a step.

In a possible embodiment, the thermal image is obtained by continuous measurements e.g. by scanning along a line, e.g. in a transverse direction over the grain-MOG mixture path in embodiments in which the grain-MOG mixture is moved along a grain-MOG mixture path, or by taking a thermal image of an area of the grain-MOG mixture.

In a possible embodiment multiple thermal images are taken, e.g. in a intermittent way.

The scanning along a line in a transverse direction over the grain-MOG mixture path can alternatively optionally be carried out in an intermittent way.

In a possible embodiment, an ambient temperature is present in the vicinity of the grain-MOG mixture, and the thermal excitation results in the sample volume obtaining a surface temperature that is different from the ambient temperature. In this embodiment, the surface temperature of the sample volume changes or is allowed to change towards the ambient temperature during the time between the thermal excitation and the generation of the thermal image, e.g. during the transfer from the thermal excitation location to the imaging location.

In an example of this embodiment, for example the sample volume is heated up during the thermal excitation, and then allowed to cool somewhat before the thermal image is generated. Due to their mutual difference in heat capacity the kernels and the material other than grain do not only heat up at a mutually different rate, but they also cool down at a mutually different rate. Depending on the exact curves for the temperature changes over time given a certain heat input and difference with ambient temperature, it is possible that at a certain point in time the difference in expected temperature of the kernels and of the material other than grain, in particular of the chaff, is larger during the cooling down period than during the warming up period. It is advantageous to generate the thermal image when the expected temperature difference between the kernels and the material other than grain is the largest, because then the best distinction between the two can be made.

Of course, a similar situation may occur when the sample volume is cooled during the thermal excitation, and then allowed to heat up somewhat before the thermal image is generated.

In a possible embodiment, the thermal excitation involves heating of the sample volume, using at least one of air of an elevated temperature, a halogen heat source, an infrared heat source, an inductive heat source, an electrical resistance heat source, microwaves, or friction heat e.g. induced by vibrations to which the sample volume is subjected.

In a possible embodiment, the thermal excitation involves cooling of the sample volume, using at least one of air of a reduced temperature or a peltier element.

In a possible embodiment, the thermal excitation involves both cooling and heating of the sample volume of the grain-MOG mixture.

In a possible embodiment, the thermal image is generated using reflection. In an alternative embodiment, the thermal image is generated using transmission. In an alternative embodiment, the thermal image is generated using reflection and transmission.

In a possible embodiment, the grain-MOG mixture further comprises a chaff fraction, and the method further comprises the step of relating the temperature distribution to the share of the chaff fraction in the grain-MOG mixture.

In this embodiment, this is for example done by obtaining the percentage of the total area of the thermal image that has a temperature that generally corresponds to the temperature that—given the amount of transferred thermal energy in the thermal excitation—can be expected for the chaff. So, in this embodiment, the share of the kernel fraction and the share of the chaff fraction in the total sample volume of the grain-MOG mixture are obtained independently from each other.

In a possible embodiment, the kernel fraction comprises a clean kernel subfraction and a white caps subfraction, and the share of the white caps subfraction is determined based on a combination of the thermal imaging and optical imaging.

The heat capacity of clean kernels, not being encapsulated in chaff anymore and the heat capacity of whitecaps are very similar which makes them hard to distinguish from each other using a thermal method e.g. as in accordance with the invention; clean kernels and whitecaps will look generally the same on a thermal image.

On the other hand, with optical methods as for example described in US2009/0297040, whitecaps will look generally the same as chaff, because a whitecap has chaff material at its outer surface.

By combining the method according to the invention and an optical method, e.g. the optical method of US2009/0297040, the share of whitecaps in the grain-MOG mixture can be determined. In the thermal method according to an aspect of the present invention, the share of the whitecaps subfraction will be incorporated in the result for the share of the overall kernel fraction. In the result of the optical method, the share of the whitecaps subfraction will be incorporated in the share of the chaff fraction.

For example, say that the thermal method gives a result of 97% kernel fraction and 3% chaff fraction, and the optical method gives a result of 95% kernel fraction and 5% chaff fraction, the whitecaps subfraction will be 2%.

In a variant, the thermal method further comprises the step of relating the temperature distribution to the share of the chaff fraction in the grain-MOG mixture so the share of the kernel fraction and the share of the chaff fraction in the total sample volume of the grain-MOG mixture are obtained independently from each other by thermal imaging.

In a possible embodiment, during the thermal excitation, thermal energy is transferred by the thermal excitator to the sample volume of the grain-MOG mixture in a modulated way, in the form of a pulse, in the form of a square pulse, in the form of a sinusoidal wave, or in the form of a step.

In accordance with another aspect of the present invention, there is provided a device for analyzing the composition of a grain-MOG-mixture. The device comprises a grain-MOG mixture composition sensor. The grain-MOG mixture composition sensor of the agricultural harvester comprises a thermal excitator, being arranged at a thermal excitation location and being adapted to subject a sample volume of the grain-MOG mixture to a thermal excitation, a thermal imaging device, being adapted to generate a thermal image at an imaging location of at least a surface of the sample volume of the grain-MOG mixture that has been subjected to the thermal excitation, an image processing device, being adapted to process the thermal image obtained by the thermal imaging device to obtain data representing the temperature distribution over the thermal image, and to relate the temperature distribution to the share of the kernel fraction and/or of the MOG-fraction in the grain-MOG mixture.

In a possible embodiment, the thermal imaging device is adapted to generate multiple subsequent thermal images of at least a surface of the sample volume of the grain-MOG mixture that has been subjected to the thermal excitation.

In a possible embodiment, the grain-MOG mixture composition sensor comprises multiple thermal imaging devices.

In a possible embodiment, the imaging location and the thermal excitation location coincide with each other.

In a possible embodiment, the thermal excitator is adapted to transfer the thermal energy during the thermal excitation the sample volume of the grain-MOG mixture in a modulated way, in the form of a pulse, in the form of a square pulse, in the form of a sinusoidal wave, or in the form of a step.

In a possible embodiment, the thermal imaging device is adapted to obtain the thermal image by continuous measurements e.g. by scanning along a line, e.g. in a transverse direction over a grain-MOG mixture path, or by taking a thermal image of an area of the grain-MOG mixture travelling.

For example, the thermal imaging device is a thermal line scanner or a thermal camera.

In a possible embodiment, multiple thermal images are taken, e.g. in an intermittent way.

In a possible embodiment, the thermal excitator and thermal imaging device are arranged along a grain-MOG mixture path.

Optionally, the thermal imaging device is arranged spaced apart from and downstream of the thermal excitator seen in the direction of conveyance of the grain-MOG mixture along a grain-MOG mixture path.

In a possible embodiment, the device according to exemplary embodiments of the present invention further comprises an optical imaging device. Optionally, the optical imaging device is an optical imaging device in accordance with US2009/0297040.

Optionally, the image processing device is adapted to process data from the thermal imaging device and from the optical imaging device, and to process this data in a combined way to determine the share of a white caps subfraction in the kernel fraction.

In a possible embodiment, the thermal excitator comprises at least one of at least one of a halogen heat source, an infrared heat source, an inductive heat source, an electrical resistance heat source, a microwaves source, or friction heat generator, a peltier element, a source of air of a reduced temperature.

In a possible embodiment, the device according to exemplary embodiments of the present is arranged at a grain storage facility.

In accordance with yet another aspect of the present invention, there is provided an agricultural harvester comprising a crop inlet, a processing device which is adapted and arranged to receive harvested crop from the crop inlet, said processing device comprising a thresher, a grain-MOG mixture discharge and a waste discharge, wherein the processing device is adapted to thresh the harvested crop to obtain a grain-MOG mixture comprising a kernel fraction, a grain tank adapted for accommodating said grain-MOG mixture, said grain tank having a grain tank inlet, a grain conveyor assembly, extending between the grain-MOG mixture discharge and the grain tank inlet along a grain-MOG mixture path, which is adapted to convey the grain-MOG mixture from the grain-MOG mixture discharge to the grain tank inlet along said grain-MOG mixture path, and a device for analyzing the composition of a grain-MOG mixture in accordance with an exemplary embodiment of the present invention.

Optionally, the agricultural harvester is a combine harvester.

Optionally, the agricultural harvester is a thresher device, either a mobile thresher device or a stationary thresher device.

The method in accordance with aspects of the present invention can advantageously be applied in an agricultural harvester that comprises a thresher and optionally a sieve device and/or other separator device adapted to separate kernels from loose chaff By monitoring the grain-MOG mixture that leaves the thresher and/or sieve device using the method in accordance with an aspect of the present invention, the threshing performance and/or sieving performance can be measured and/or monitored. Optionally, the results of the measuring and/or monitoring obtained by the method can be used to control the threshing and/or the sieving.

In a possible embodiment, the grain conveyor assembly comprises a grain elevator, optionally including a grain elevator bypass, and the thermal excitator and the thermal imaging device are arranged at the grain elevator, optionally at the grain elevator bypass.

Optionally, a thermal excitator and thermal imaging device of the grain-MOG mixture composition sensor and the optical imaging device are arranged at the grain elevator, optionally at a grain elevator bypass of the agricultural harvester.

In a possible embodiment, the agricultural harvester comprises an engine, and the thermal excitator comprises a duct which is adapted to accommodate air that has been heated by said engine. The heated air can then be used as a heat source by the thermal excitator.

BRIEF DESCRIPTION OF THE DRAWINGS

For the purpose of illustration, there are shown in the drawings certain embodiments of the present invention. It should be understood, however, that the invention is not limited to the precise arrangements, dimensions, and instruments shown. Like numerals indicate like elements throughout the drawings. In the drawings.

DETAILED DESCRIPTION OF THE INVENTION

Figure 1A:
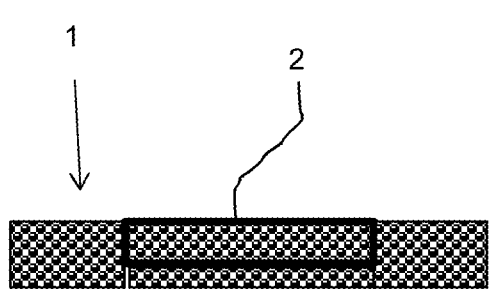
FIGS. 1A-1C illustrate an embodiment of a method, in accordance with an exemplary embodiment of the present invention.
Figure 1B:
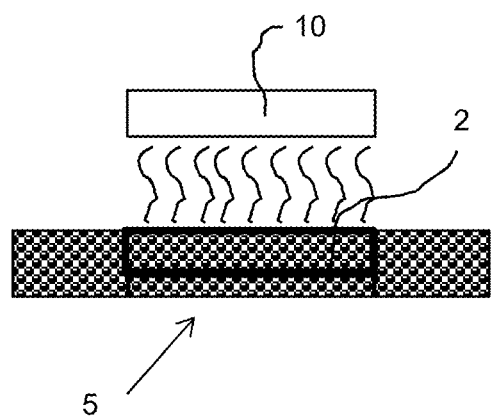
Figure 1C:
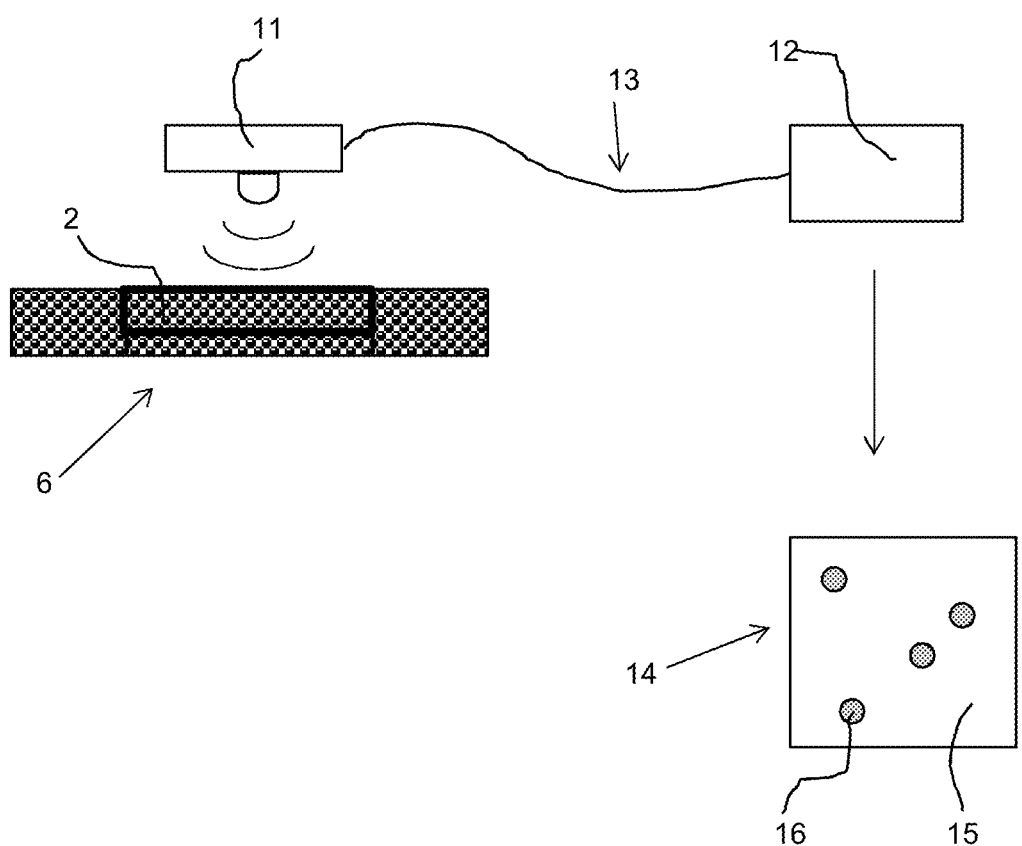

FIGS. 1A-1C illustrate an embodiment of a method, in accordance with an exemplary embodiment of the present invention.

FIG. 1A shows a grain-MOG mixture 1 containing a sample volume 2. In this embodiment, the sample volume 2 is a part of the total volume of the grain-MOG mixture 1.

FIG. 1B shows a next step in the method. At a thermal excitation location 5, the sample volume 2 of the grain-MOG mixture 1 is subjected to a thermal excitation, e.g. heating or cooling. A thermal excitator 10 is provided to carry out the thermal excitation.

FIG. 1C shows a further step in the method. A thermal image 14 is generated at an imaging location 6. The thermal excitation location 5 and the thermal imaging location 6 may coincide with each other. The thermal image 14 is generated of at least a surface of the sample volume 2 of the grain-MOG mixture 1 that has been subjected to the thermal excitation. The thermal image 14 is generated by a thermal imaging device 11. The thermal image 14 is processed by an image processor 12 that receives data from the thermal imaging device 11 via data connection 13. The data connection 13 can be a wired connection or a wireless connection.

The thermal image 14 is processed and therewith data representing the temperature distribution over the thermal image 14 is obtained. In the example of FIG. 1C, this results in a thermal image 14 which shows a generally uniform background color 15, and some spots 16 with a different temperature. Optionally, multiple thermal images are generated, e.g. intermittently, in order to monitor the temperature change over time within the sample volume 2.

The subsequent step in the method is to relate the temperature distribution to the share of the kernel fraction in the grain-MOG mixture. In the example of FIG. 1C, the background temperature 15 generally corresponds to the temperature that—given the amount of transferred thermal energy in the thermal excitation—can be expected for the kernels. The different temperature 16 generally corresponds to the temperature that—given the amount of transferred thermal energy in the thermal excitation—can be expected for chaff By calculating the percentage of the area of the thermal image 14 that has the background temperature 15, the share of the kernel fraction in the grain-MOG mixture 1 can be determined. By calculating the percentage of the area of the thermal image 14 that has the different temperature 16, the share of the chaff fraction in the grain-MOG mixture 1 can be determined.

Figure 2A:
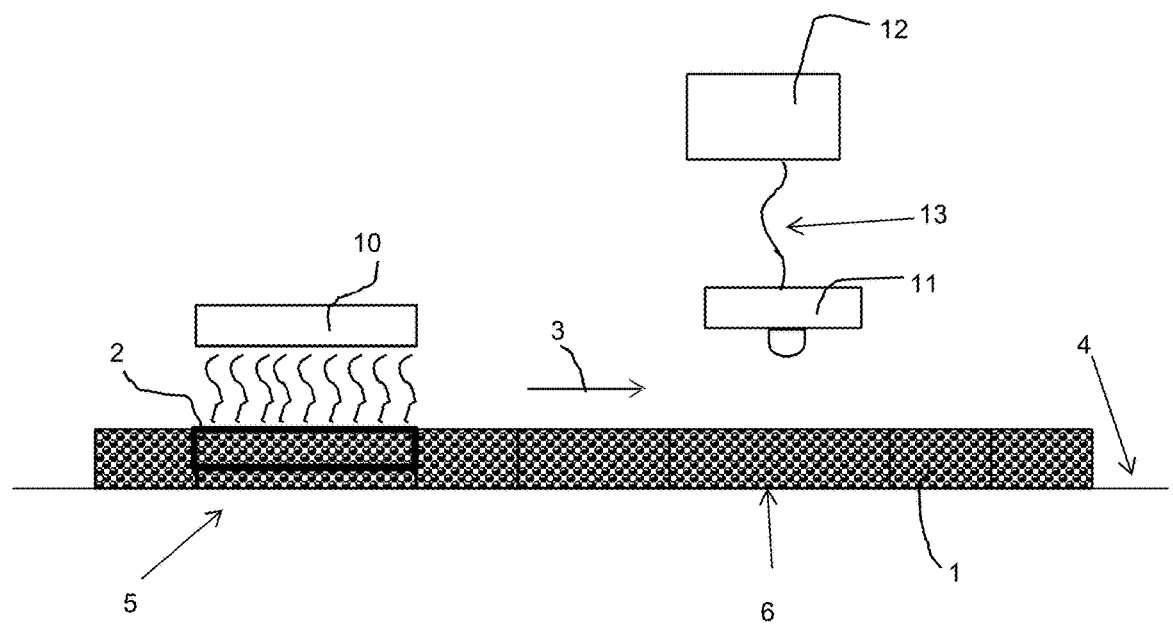
FIGS. 2A-2B illustrate a second embodiment of a method, in accordance with an exemplary embodiment of the present invention.
Figure 2B:
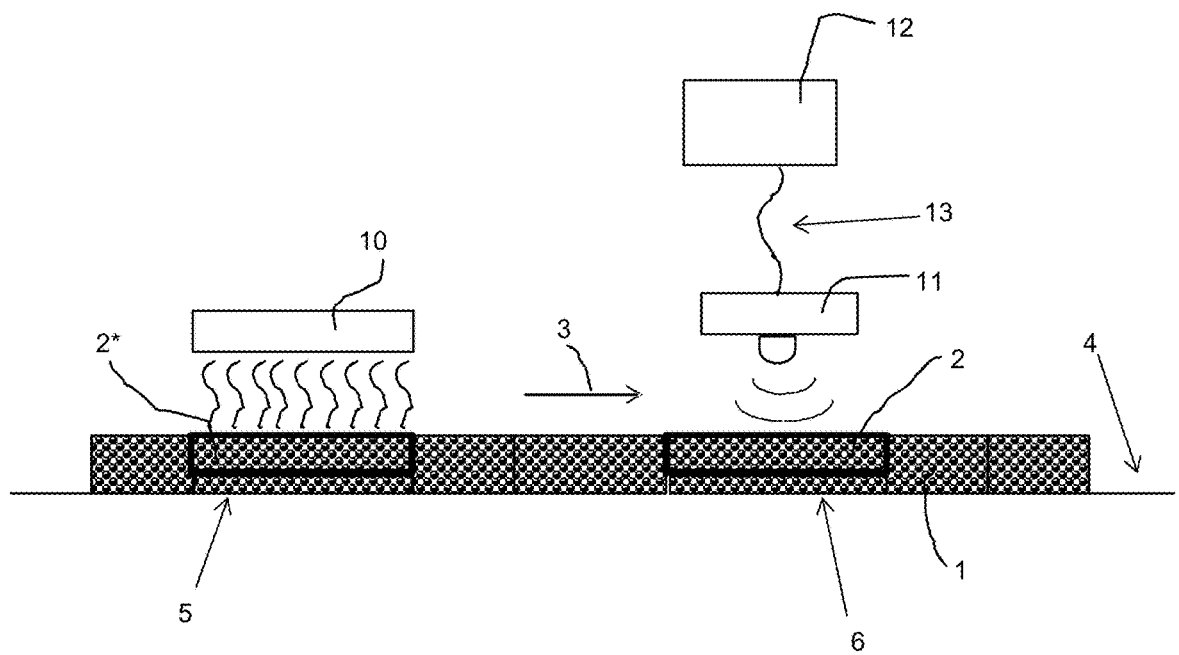

FIGS. 2A-2B illustrates a second embodiment of a method, in accordance with an exemplary embodiment of the present invention.

FIG. 2A shows a grain-MOG mixture 1 containing a sample volume 2. The grain-MOG mixture is transported in bulk form along a grain-MOG mixture path 4, in a direction of transport 3. The grain-MOG mixture 1 can move continuously or intermittently along the grain-MOG mixture path 4.

The thermal excitation location 5 and the imaging location 6 are located along the grain-MOG mixture path 4. The imaging location 6 is arranged downstream of the thermal excitation location 5, as seen in the direction of movement 3 of the grain-MOG mixture 1 along the grain-MOG mixture path 4.

At a thermal excitation location 5, the sample volume 2 of the grain-MOG mixture 1 is subjected to a thermal excitation, e.g. heating or cooling. A thermal excitator 10 is provided to carry out the thermal excitation.

Optionally the thermal energy is transferred during the thermal excitation by the thermal excitator 10 to the sample volume 2 of the grain-MOG mixture in a modulated way, in the form of a pulse, in the form of a sinusoidal wave, in the form of a square pulse or in the form of a step.

In FIG. 2A, the sample volume 2 is a discreet sample volume, so upstream and downstream of the sample volume 2, there is grain-MOG mixture which is not subjected to the thermal excitation. This can for example be achieved by intermittent activation of the thermal excitator 10. It is however alternatively possible that the grain-MOG mixture does not contain discrete sample volumes.

FIG. 2B shows that the sample volume 2 has moved along the grain-MOG mixture path 4 and has now reached the imaging location 6. Meanwhile, a next sample volume 2* has arrived at the thermal excitation location 5.

At imaging location 6, a thermal image is generated. The thermal image is generated of at least a surface of the sample volume 2 of the grain-MOG mixture 1 that has been subjected to the thermal excitation. The thermal image is generated by a thermal imaging device 11. The thermal image is processed by an image processor 12 that receives data from the thermal imaging device 11 via data connection 13. The data connection 13 can be a wired connection or a wireless connection. The thermal image can be obtained using reflection, transmission or a combination of reflection and transmission.

The thermal image is processed and therewith data representing the temperature distribution over the thermal image is obtained.

The subsequent step in the method is to relate the temperature distribution to the share of the kernel fraction in the grain-MOG mixture. This can be done in the same way as is described in relation to the embodiment of FIGS. 1A-1C.

In the embodiment of FIGS. 2A-2B, the thermal excitation location 5 is spaced apart from the imaging location 6.

If the thermal excitation results in the sample volume 2 obtaining a surface temperature that is different from the ambient temperature in the vicinity of the grain-MOG mixture path 4, the surface temperature of the sample volume 2 will change towards the ambient temperature during the time between the thermal excitation and the generation of the thermal image if no measures are taken to prevent this.

This can be advantageous. Due to their mutual difference in heat capacity, the kernels and the material other than grain do not only heat up at a mutually different rate, but they also cool down at a mutually different rate. Depending on the exact curves for the temperature changes over time given a certain heat input and difference with ambient temperature, it is possible that at a certain point in time the difference in expected temperature of the kernels and of the material other than grain, in particular of the chaff, is larger during the cooling down period than during the warming up period. It is advantageous to generate the thermal image when the expected temperature difference between the kernels and the material other than grain is the largest, because then the best distinction between the two can be made.

In a variant of the embodiment of FIGS. 2A-2B, the grain-MOG-mixture is not moved along a grain-MOG path. Instead, the grain-MOG mixture remains stationary during the analysis. In this variant, the thermal excitation location 5 and the thermal imaging location 6 coincide with each other. Desirably, multiple thermal images of the sample volume are generated over time, so that the response of the kernel fraction and/or the MOG fraction over time to the thermal excitation can be obtained. This increases the accuracy and reliability of the analysis, as the kernels and the MOG show a different temperature profile in response to thermal excitation.

Figure 3:
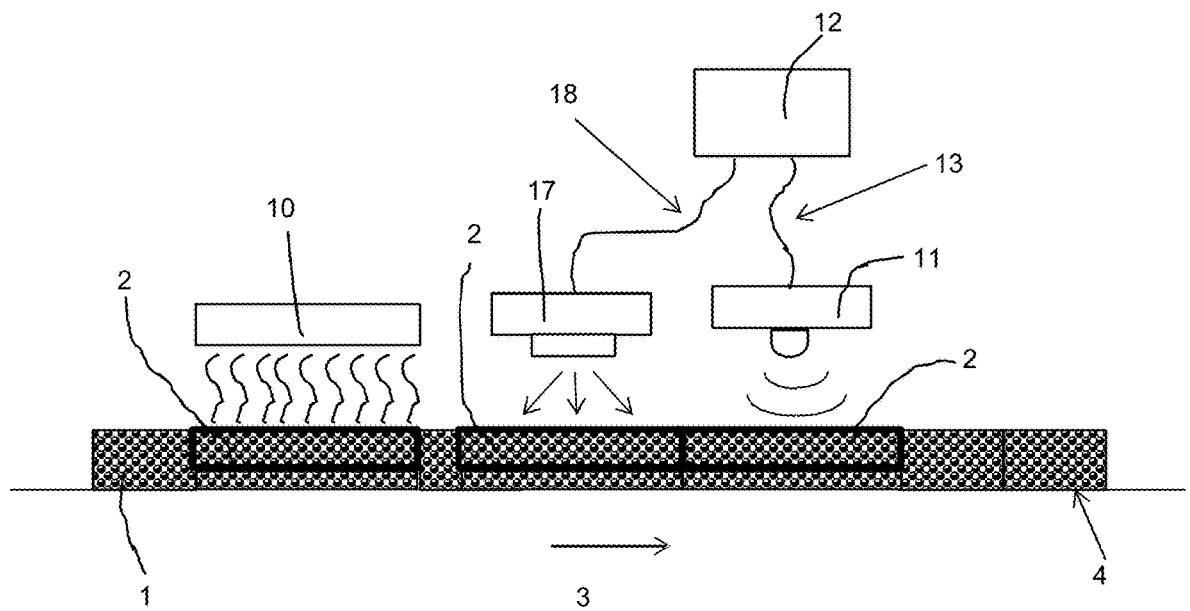
FIG. 3 illustrates a third embodiment of a method, in accordance with an exemplary embodiment of the present invention.

FIG. 3 illustrates a third embodiment of a method, in accordance with an exemplary embodiment of the present invention.

The embodiment of FIG. 3 is similar to the embodiment of FIGS. 2A-2B. The difference is that an optical imaging device 17 is provided in addition to the thermal excitator 10 and the thermal imaging device 11. The optical imaging device 17 is connected to the image processor via data connection 18. Data connection 18 can be a wired connection or a wireless connection.

In the embodiment of FIG. 3, a sample volume 2 is subjected to a thermal excitation followed by the generation of a thermal image in the same way as was described in relation to the embodiments of FIGS. 1A-1C and FIGS. 2A-B. In addition, an optical analysis is carried out on the sample volume 2, e.g. in accordance with US2009/0297040. The optical analysis can be carried out prior to the thermal excitation, after the thermal imaging or between the thermal excitation and the thermal imaging or simultaneously with the thermal imaging.

The results of the thermal imaging and the optical analysis are combined in order to detect whitecaps.

The heat capacity of clean kernels, not being encapsulated in chaff anymore and the heat capacity of whitecaps are very similar which makes them hard to distinguish from each other using a thermal method, e.g., because clean kernels and whitecaps will look generally the same on a thermal image.

On the other hand, with optical methods as for example described in US2009/0297040, whitecaps will look generally the same as chaff, because a whitecap has chaff material at its outer surface.

By combining the method according to exemplary embodiments of the present invention and an optical method, e.g. the optical method of US2009/0297040, the share of whitecaps in the grain-MOG mixture can be determined. In the thermal method according to exemplary embodiments of the present invention, the share of the whitecaps subfraction will be incorporated in the result for the share of the overall kernel fraction. In the result of the optical method, the share of the whitecaps subfraction will be incorporated in the share of the chaff fraction.

Figures 4A, 4B, 4C:
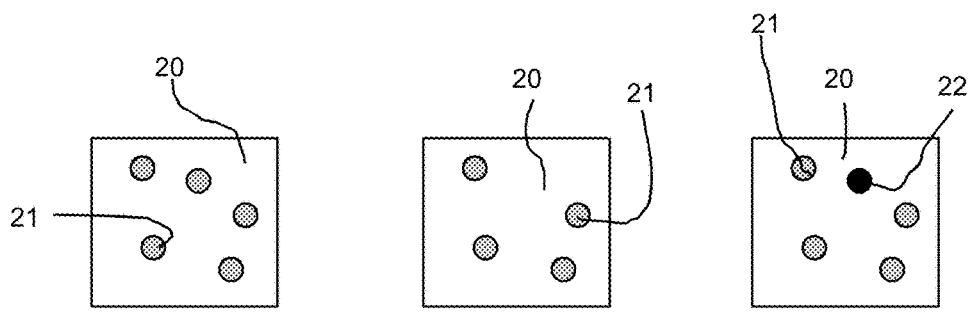
FIGS. 4A-4C illustrate a combination of thermal and optical imaging, in accordance with an exemplary embodiment of the present invention.

FIGS. 4A-4C illustrate a combination of thermal and optical imaging for the detection of whitecaps, in accordance with an exemplary embodiment of the present invention.

FIG. 4A shows an example of an image of a sample volume 2 that is obtained using optical imaging, e.g. using the method of US2009/0297040. The white background area 20 is recognized as being the kernel fraction of the grain-MOG mixture, while the grey circles 21 schematically indicate regions being recognized as chaff FIG. 4B shows an example of an image of a sample volume 2 that is obtained using thermal imaging in accordance with exemplary embodiments of the present invention. The white background area 20 is recognized as being the kernel fraction of the grain-MOG mixture, while the grey circles 21 schematically indicate regions being recognized as chaff Comparing the images of FIG. 4A and FIG. 4B, it is clear that there is an area at the top right of the image that the optical imaging method designates as chaff and the thermal imaging method designates as kernels. As explained above, this is an indication that very likely whitecaps are present there.

FIG. 4C shows the result of the combined analysis: the white background area 20 represents the kernel fraction, the grey circles 21 represent chaff and the black circle 22 represents the whitecaps.

Of course, FIGS. 4A-4C are very schematic representations, as in reality the images will be much more detailed, possibly even up to the level of showing individual grains.

Figure 5:
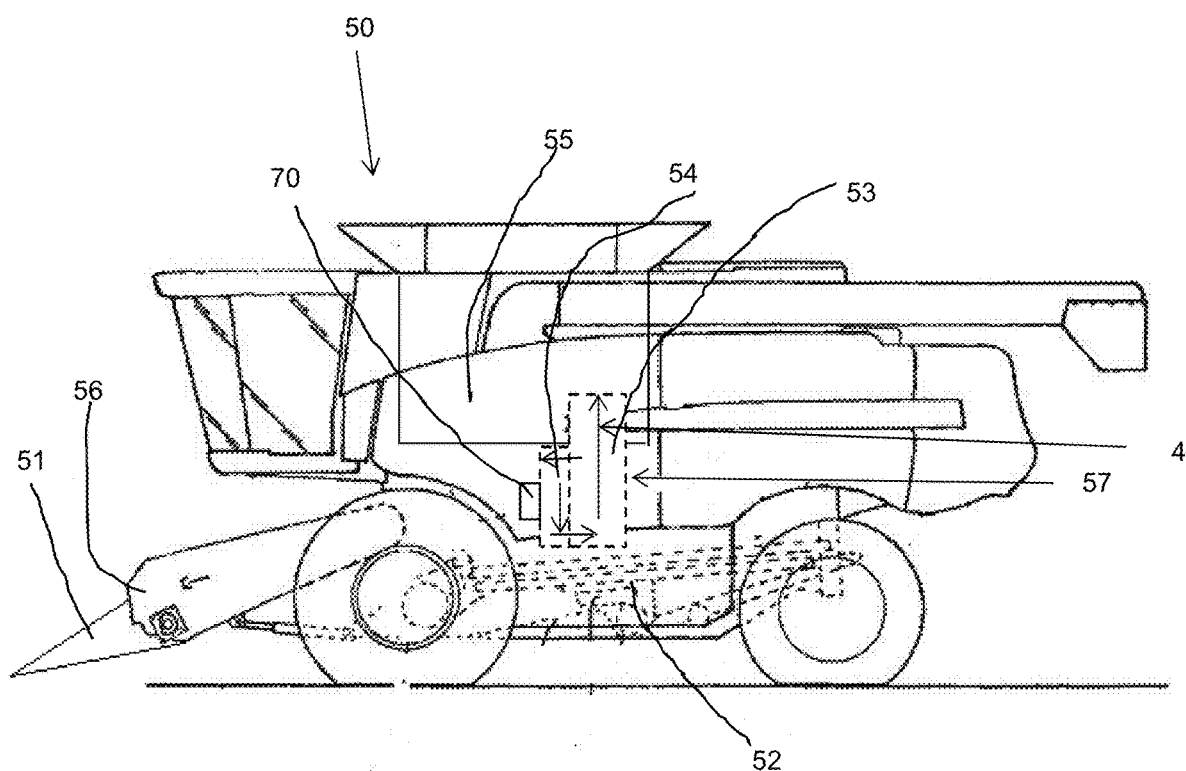
FIG. 5 illustrates a combine harvester in which a method according to an exemplary embodiment of the invention can be applied.

FIG. 5 illustrates a combine harvester 50 in which a method in accordance with an exemplary embodiment of the present invention can be applied.

The combine harvester 50 comprises a header 51 for harvesting crop, e.g. by cutting it loose from the field. The harvester crop is collected and transported internally via a crop inlet 56 to a processing device 52 inside the combine harvester 50.

The processing device 52 which is adapted and arranged to receive harvested crop from the crop inlet 56. The processing device 52 comprises a thresher, a grain-MOG mixture discharge and a waste discharge (see FIG. 6). The processing device 52 is adapted to thresh the harvested crop to obtain a grain-MOG mixture comprising a kernel fraction. In addition, the processing unit may comprise a separation unit and/or a cleaning unit.

The combine harvester further comprises a grain tank 55 adapted for accommodating the grain-MOG mixture.

The combine harvester further comprises a grain conveyor assembly 57, extending between the grain-MOG mixture discharge and the grain tank inlet along a grain-MOG mixture path 4. The grain conveyor assembly 57 is adapted to convey the grain-MOG mixture from the grain-MOG mixture discharge to the grain tank inlet along the grain-MOG mixture path 4.

In the example of FIG. 5, the grain conveyor assembly 57 comprises a grain elevator 53 and a grain elevator bypass 54. Grain-MOG mixture is withdrawn from the grain elevator and drops through the grain elevator bypass 54 to a lower level than the level at which it was withdrawn from the grain elevator 53, and is then re-introduced into the grain elevator 53. The grain-MOG mixture in the grain elevator bypass 54 can for example be used to determine or monitor parameters of the grain-MOG mixture leaving the processing device 52. The grain-MOG mixture path 4 has a branch that extends through the grain elevator bypass 53.

The combine harvester 50 as shown in FIG. 5 further comprises a grain-MOG mixture composition sensor 70 with is adapted to determine the share of the kernel fraction in the grain-MOG mixture in accordance with a method according to an exemplary embodiment of the present invention.

Figure 6:
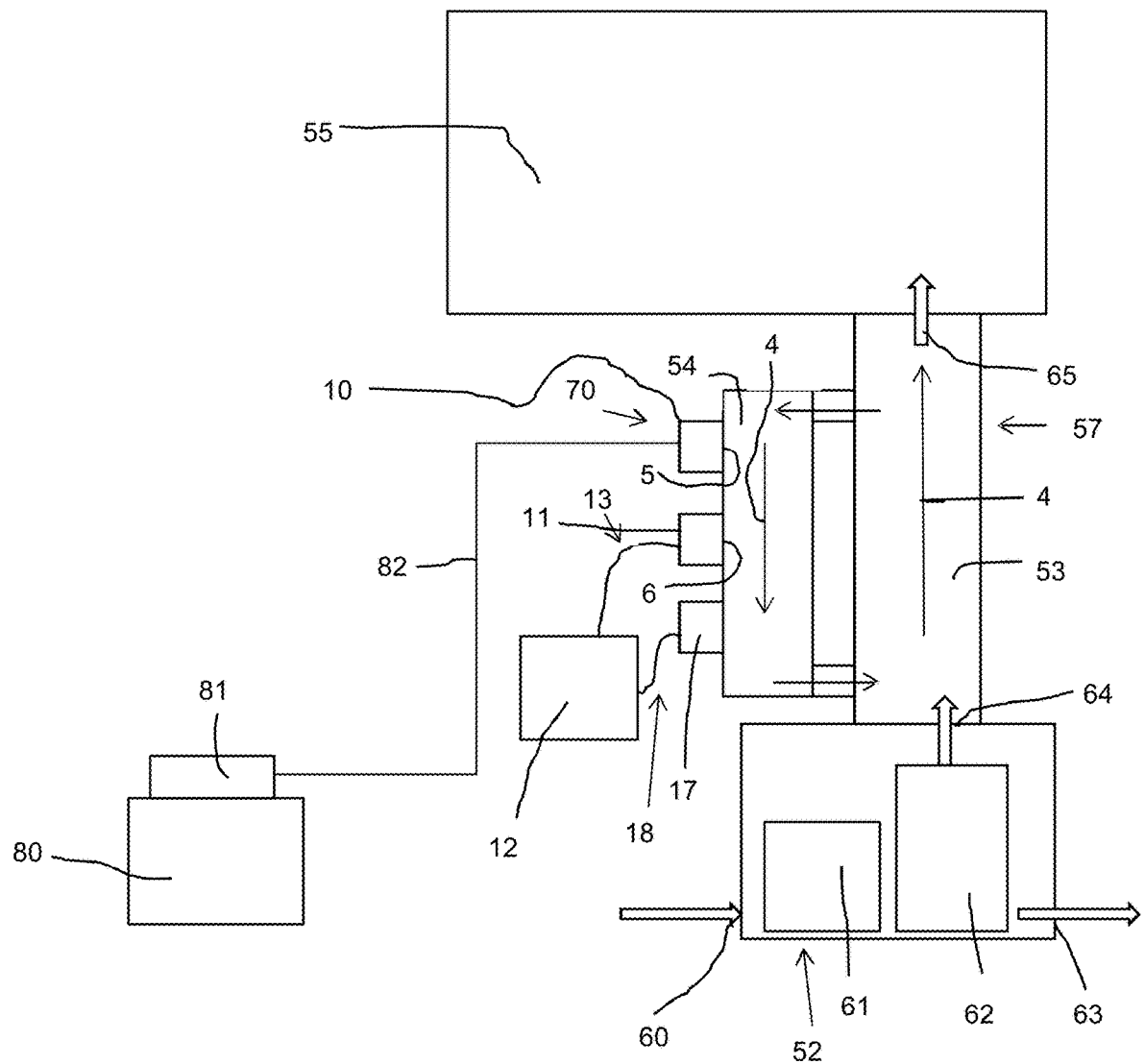
FIG. 6 illustrates an embodiment of an agricultural harvester, in accordance with an exemplary embodiment of the present invention.

FIG. 6 schematically illustrates an embodiment of an agricultural harvester, in accordance with an exemplary embodiment of the present invention. The elements shown in FIG. 6 could be arranged for example in the combine harvester of FIG. 5.

The agricultural harvester of FIG. 6 comprises a crop inlet 60. A processing device 52 is present which is adapted and arranged to receive harvested crop from the crop inlet 60. The processing device 52 comprises a thresher 61, optionally combined with a separation unit and/or a cleaning unit 62, a grain-MOG mixture discharge 64 and a waste discharge 63. The processing device 52 is adapted to thresh the harvested crop to obtain a grain-MOG mixture comprising a kernel fraction and an MOG-fraction.

The agricultural harvester further comprises a grain tank 55 adapted for accommodating said grain-MOG mixture. The grain tank 55 has a grain tank inlet 65.

The agricultural harvester according to the example of FIG. 6 further comprises a grain conveyor assembly 57, extending between the grain-MOG mixture discharge 64 and the grain tank inlet 65 along a grain-MOG mixture path 4. The grain conveyor assembly 57 is adapted to convey the grain-MOG mixture from the grain-MOG mixture discharge 64 to the grain tank inlet 65 along said grain-MOG mixture path 4.

In the example of FIG. 6, the grain conveyor assembly 57 comprises a grain elevator 53 and a grain elevator bypass 54. Grain-MOG mixture is withdrawn from the grain elevator and drops through the grain elevator bypass 54 to a lower level than the level at which it was withdrawn from the grain elevator 53, and is then re-introduced into the grain elevator 53. The grain-MOG mixture in the grain elevator bypass 54 can for example be used to determine or monitor parameters of the grain-MOG mixture leaving the processing device 52. The grain-MOG mixture path 4 has a branch that extends through the grain elevator bypass 53.

The agricultural harvester according to the example of FIG. 6 further comprises a grain-MOG mixture composition sensor 70 with is adapted to determine the share of the kernel fraction and/or the MOG-fraction in the grain-MOG mixture in accordance with a method according to an exemplary embodiment of the present invention.

In the example of FIG. 6, the grain-MOG mixture composition sensor 70 comprises a thermal excitator 10, a thermal imaging device 11 and an image processing device 12. The thermal excitator 10 is arranged at a thermal excitation location 5 and is adapted to subject a sample volume of the grain-MOG mixture to a thermal excitation.

The thermal excitator 10 may be adapted to transfer the thermal energy during the thermal excitation the sample volume of the grain-MOG mixture in a modulated way, in the form of a pulse, in the form of a square pulse, in the form of a sinusoidal wave, or in the form of a step.

The thermal imaging device 11 is adapted to generate a thermal image at an imaging location 6 of at least a surface of the sample volume of the grain-MOG mixture that has been subjected to the thermal excitation. The thermal imaging device 11 may be for example a thermal line scanner or a thermal camera.

The thermal imaging device 11 may be adapted to obtain the thermal image by scanning along a line in a transverse direction over the grain-MOG mixture path 4, or by taking a thermal image of an area of the grain-MOG mixture travelling on the grain-MOG mixture path 4, e.g. taking multiple thermal images in a intermittent way.

The image processing device 12 is adapted to process the thermal image obtained by the thermal imaging device 11 to obtain data representing the temperature distribution over the thermal image, and to relate the temperature distribution to the share of the kernel fraction in the grain-MOG mixture.

In the example of FIG. 6, the thermal imaging device 11 is arranged spaced apart from and downstream of the thermal excitator seen 10 in the direction of conveyance of the grain-MOG mixture along the grain-MOG mixture path 4.

In the embodiment of FIG. 6, the thermal excitator 10 and the thermal imaging device 11 are arranged at the grain elevator bypass 54 of the grain elevator 53.

In the embodiment of FIG. 6, an optical imaging device 17 is provided. It is connected to the image processing device 12 by data connection 18, which may be a wired or wireless connection. The image processing device 12 is adapted to process data from the thermal imaging device 11 and from the optical imaging device 17, and to process this data in a combined way to determine the share of a white caps subfraction in the kernel fraction.

In FIG. 6, the optical imaging device 17 is shown as being arranged downstream of the thermal imaging device 11. Optionally, the optical imaging device 17 is arranged such that the thermal imaging device 11 and the optical imaging device 11 simultaneously generate an image of the same sample volume. This increases the accuracy and reliability of the analysis.

In the embodiment of FIG, 6, the agricultural harvester comprises an engine 80, e.g. a combustion engine. The engine generates heat while it is running. This generated het can be used in the thermal excitation to heat up the sample volume of the grain-MOG mixture to be evaluated.

In the example of FIG. 6, a collection header 81 is provided at a heated surface of the engine. In the header 81, air is accommodated and heated by the heat that is generated by the engine. A duct 82 accommodates the heated air and takes the heated air from the header 81 to the thermal excitator 10. A fan or the like can be provided to effect this flow of heated air from the header 81 to the thermal excitator 10.

Alternatively or in addition, the thermal excitator 10 comprises at least one of a halogen heat source, an inductive heat source, an infrared heat source, an electrical resistance heat source, a microwaves source, or friction heat generator, a peltier element, a source of air of a reduced temperature.

In a variant of the embodiment of FIG. 6, the grain-MOG mixture in the grain elevator is kept stationary during the analysis by the grain-MOG mixture composition sensor.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A method for analyzing harvested crop, the method comprising steps of:
    receiving a grain-MOG mixture comprising a kernel fraction and an MOG-fraction;
    at a thermal excitation location, subjecting a sample volume of the grain-MOG mixture to a thermal excitation using a thermal excitatory thereby transferring thermal energy to or from the grain-MOG mixture;
    stopping the thermal excitation;
    waiting a predetermined amount of time after the stopping step thereby allowing a temperature difference to develop between the kernel fraction and the MOG-fraction;
    generating a thermal image at an imaging location after the waiting step, after the thermal energy has been transferred to the grain-MOG mixture, of at least a surface of the sample volume of the grain-MOG mixture that has been subjected to the thermal excitation;
    processing the thermal image and therewith obtaining data representing a temperature distribution over the thermal image; and
    relating the temperature distribution to a share of the kernel fraction or to the MOG-fraction in the grain-MOG mixture.

2. The method according to claim 1, further comprising a step of generating multiple subsequent thermal images of at least a surface of the sample volume of the grain-MOG mixture that has been subjected to the thermal excitation.

3. The method according to claim 1, wherein the imaging location and the thermal excitation location coincide with each other, and wherein the steps of subjecting and generating are performed simultaneously.

4. The method according to claim 1, wherein:
    an ambient temperature is present in the vicinity of the grain-MOG mixture,
    the thermal excitation results in the sample volume obtaining a surface temperature that is different from the ambient temperature, and
    the surface temperature of the sample volume changes towards the ambient temperature during a time between performance of the step of subjecting and performance of the step of generating.

5. The method according to claim 1,
    wherein the step of subjecting comprises heating the sample volume using at least one of air of an elevated temperature, a halogen heat source, an infrared heat source, an inductive heat source, an electrical resistance heat source, microwaves, and a friction heat, or
    wherein the step of subjecting comprises cooling the sample volume using at least one of air of a reduced temperature or a peltier element.

6. The method according to claim 1, wherein the grain-MOG mixture further comprises a chaff fraction, and wherein the method further comprises a step of relating the temperature distribution to a share of the chaff fraction in the grain-MOG mixture.

7. The method according to claim 6, wherein the kernel fraction comprises a clean kernel subfraction and a white caps subfraction, and wherein the method further comprises a step of determining a share of the white caps subfraction based on a combination of the thermal image and optical imaging.

8. The method according to claim 1, wherein the thermal excitation is carried out in a modulated way, in the form of a pulse, in the form of a square pulse, in the form of a sinusoidal wave, or in the form of a step.

9. A device for analyzing harvested crop, the device comprising a sensor comprising:
    a thermal excitator arranged at a thermal excitation location, the thermal excitator adapted to subject a sample volume of a grain-MOG mixture to a thermal excitation thereby transferring thermal energy to the grain-MOG mixture, the grain-MOG mixture comprising a kernel fraction and an MOG-fraction;
    a thermal imaging device adapted to generate a thermal image at an imaging location of at least a surface of the sample volume of the grain-MOG mixture after waiting a predetermined amount of time after the grain-MOG mixture has stopped receiving the thermal energy due to the thermal excitation, thereby allowing a temperature difference to develop between the kernel fraction and the MOG-fraction; and
    an image processing device adapted to process the thermal image obtained by the thermal imaging device to obtain data representing a temperature distribution over the thermal image, and to relate the temperature distribution to a share of the kernel fraction or the MOG-fraction in the grain-MOG mixture.

10. The device according to claim 9, wherein the thermal imaging device is further adapted to generate multiple subsequent thermal images of at least a surface of the sample volume of the grain-MOG mixture that has been subjected to the thermal excitation.

11. The device according to claim 9, wherein the grain-MOG mixture composition sensor further comprises multiple thermal imaging devices.

12. The device according to claim 9, wherein the imaging location and the thermal excitation location coincide with each other.

13. The device according to claim 9, further comprising an optical imaging device.

14. The device according to claim 13, wherein the image processing device is further adapted to process data from the thermal imaging device and from the optical imaging device, and to process the data from the thermal imaging device and from the optical imaging device in a combined way to determine the share of a white caps subfraction in the kernel fraction.

15. The device according to claim 9, wherein the thermal excitator comprises at least one of a halogen heat source, an infrared heat source, an inductive heat source, an electrical resistance heat source, a microwaves source, a friction heat generator, a peltier element, and a source of air of a reduced temperature.

16. The device according to claim 9, wherein the thermal excitator is adapted to carry out the thermal excitation in a modulated way, in the form of a pulse, in the form of a square pulse, in the form of a sinusoidal wave, or in the form of a step.

17. The device according to claim 9, wherein the thermal imaging device is further adapted to obtain the thermal image by scanning along a line, or by, in an intermittent way, taking a thermal image of an area of the grain-MOG mixture.

18. An agricultural harvester, comprising:
   a crop inlet;
   a processing device adapted and arranged to receive harvested crop from the crop inlet, the processing device comprising a thresher, a grain-MOG mixture discharge, and a waste discharge, the processing device further adapted to thresh the harvested crop to obtain a grain-MOG mixture comprising a kernel fraction and an MOG-fraction;
   a grain tank adapted for accommodating the grain-MOG mixture, the grain tank having a grain tank inlet;
   a grain conveyor assembly extending between the grain-MOG mixture discharge and the grain tank inlet along a grain-MOG mixture path, the grain conveyor assembly adapted to convey the grain-MOG mixture from the grain-MOG mixture discharge to the grain tank inlet along the grain-MOG mixture path;
   a device for analyzing the composition of the grain-MOG mixture according to claim 9.

19. The agricultural harvester according to claim 18, wherein the grain conveyor assembly comprises a grain elevator, and wherein the thermal excitator and the thermal imaging device are arranged at the grain elevator.

20. The agricultural harvester according to claim 18, further comprising an engine, and wherein the thermal excitator comprises a duct which is adapted to accommodate air that has been heated by the engine.

\* \* \* \* \*